United States Patent [19]

Pombo

[11] 4,263,226

[45] Apr. 21, 1981

[54] PROCESS FOR HYDROLYZING 5-ISOTHIOCYANO-5,6-DIHYDRO-DICYCLOPENTADIENE

[75] Inventor: Melvin M. Pombo, Newark, Del.

[73] Assignee: Boots Hercules Agrochemicals Co., Wilmington, Del.

[21] Appl. No.: 114,442

[22] Filed: Jan. 22, 1980

[51] Int. Cl.³ .............................................. C07C 83/00
[52] U.S. Cl. ...................................................... 564/459
[58] Field of Search ...................................... 260/563 P

[56] References Cited

U.S. PATENT DOCUMENTS

| | | | |
|---|---|---|---|
| 3,088,977 | 5/1963 | Segel | 260/563 P |
| 3,150,183 | 9/1964 | Buntin | 260/563 P |
| 3,154,579 | 10/1964 | Flanagan | 260/563 P |
| 3,238,251 | 3/1966 | Williams | 260/563 P X |
| 3,304,167 | 2/1967 | Buntin et al. | 260/563 P X |

OTHER PUBLICATIONS

"J. Org. Chem.", 34, pp. 616–624, 1969.

*Primary Examiner*—Paul F. Shaver
*Attorney, Agent, or Firm*—Richard J. Sheridan; George H. Hopkins

[57] ABSTRACT

5-Amino-5,6-dihydro-dicyclopentadiene is prepared by reacting 5-isothiocyano-5,6-dihydro-dicyclopentadiene and an aqueous caustic medium at a temperature in excess of the melting point of 1,3-bis[5-(5,6-dihydro-dicyclopentadiene)]-2-thiourea while establishing and maintaining a pressure sufficient to maintain the water in the reaction mixture in a liquid state.

1 Claim, No Drawings

PROCESS FOR HYDROLYZING 5-ISOTHIOCYANO-5,6-DIHYDRO-DICYCLOPENTADIENE

This invention relates to the conversion of 5-isothiocyano-5,6-dihydro-dicyclopentadiene having the formula:

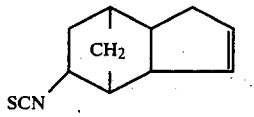
(I)

to 5-amino-5,6-dihydro-dicyclopentadiene having the formula:

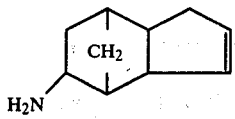
(II)

Methods for converting an organic isothiocyanate to an organic amine are disclosed in the prior art. U.S. Pat. No. 3,150,183 to Buntin discloses such a conversion by reacting the organic isothiocyanate with elementary chlorine and water in either a one- or two-step process. While Buntin does convert from isothiocyanate to amine, his process is not applicable to the present invention. Buntin's conversion process involves isothiocyanates containing an alicyclic organic radical which is a saturated hydrocarbon or a chlorohydrocarbon radical. The isothiocyanates of this invention contain an unsaturated organic radical. Thus, the use of elementary chlorine for the conversion of the isothiocyanates of this invention would lead to the undesirable loss of the unsaturation in the organic radical via attack by the chlorine.

U.S. Pat. No. 3,304,167 to Buntin and Diveley further discloses a two-step hydrolysis process for converting an isothiocyanate to an amine by first reacting the isothiocyanate with ammonia to form a thiourea and then treating the thiourea with NaOH to produce an amine.

As disclosed by Buntin and Diveley in U.S. Pat. No. 3,304,167, the hydrolysis of an isothiocyanate by caustic or related base to an amine involves the formation of a thiourea intermediate which, in the present invention, is 1,3-bis[5-(5,6-dihydro-dicyclopentadienyl)]-2-thiourea having the formula:

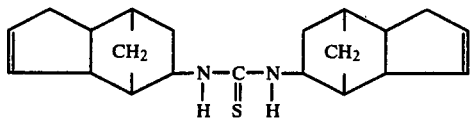
(III)

As the amine is formed during hydrolysis of the isothiocyanate, it reacts rapidly with the unreacted isothiocyanate present in the reaction mixture to form the thiourea. Due to the high insolubility of the thiourea in the aqueous reaction mixture, the reaction stops. The thiourea must then be recovered and converted to the amine.

The present invention obviates the necessity of such an involved multi-step process by providing a hydrolysis process for the conversion of 5-isothiocyano-5,6-dihydro-dicyclopentadiene to 5-amino-5,6-dihydro-dicyclopentadiene which allows the conversion to take place in a single step. This single step process comprises hydrolyzing the isothiocyanate with aqueous caustic at an elevated temperature. More particularly, the process of this invention involves the conversion of 5-isothiocyano-5,6-dihydro-dicyclopentadiene to 5-amino-5,6-dihydro-dicyclopentadiene by reacting the isothiocyanate and aqueous caustic at a temperature in excess of the melting point of the thiourea intermediate which forms during the conversion of the isothiocyanate to amine, while establishing and maintaining a pressure sufficient to maintain the water in the reaction mixture in a liquid state. By maintaining this elevated temperature, the thiourea intermediate which forms does not separate as a solid from the reaction mixture, but rather separates as a liquid which allows mixing with the caustic and thus hydrolysis of the thiourea intermediate to the amine.

The conversion from isothiocyanate to amine is accomplished in an aqueous caustic medium. The term aqueous caustic as used herein means an aqueous solution of a strongly alkaline material, such as, for example, alkali metal hydroxides. Preferred aqueous caustic media are aqueous solutions of NaOH and KOH.

The conversion of the isothiocyanate to the amine is illustrated by the following equation wherein R represents the dicyclopentadiene radical:

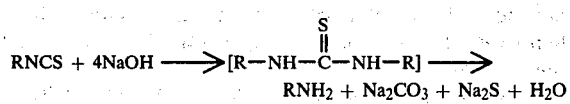

Thus, it can be seen that a molar ratio of NaOH to isothiocyanate of at least 4 to 1 is required for the conversion to be complete. Preferably, excess NaOH is used, such as, for example, a 5 to 1 molar ratio, to assure complete conversion.

The reaction temperature will generally be at least about 208° C. up to the temperature at which the reactants, intermediate or product decompose, the preferred reaction temperature being about 225° C. to about 260° C.

The pressure required for the process of this invention can be achieved by conducting the reaction in a pressure vessel, such as an autoclave. The pressure required to maintain the water in the reaction mixture in a liquid state will vary depending upon the particular temperature at which the reaction is run and the concentration of the various reactants and products present in the reaction mixture. The pressure vessel must, however, be capable of withstanding pressures in the range of about 700 p.s.i., i.e., the vapor pressure generated by pure water at about 260° C. (The actual vapor pressure of the water in the reaction mixture, however, will be lower under the conditions of this invention.) The pressure vessel must also be capable of withstanding the corrosivity of the aqueous caustic medium, nickel, or nickel-lined pressure vessels being preferred for this purpose.

The amines produced by the process of this invention are useful as chemical intermediates for the synthesis of herbicidally active compounds such as those disclosed in U.S. Pat. No. 3,304,167 to Buntin and Diveley.

The best mode contemplated of carrying out the process of this invention is illustrated by the following examples. In the examples and throughout this specification all parts and percentages are by weight unless otherwise indicated.

EXAMPLE 1

This example illustrates the single step hydrolysis of 5-isothiocyano-5,6-dihydro-dicyclopentadiene to 5-amino-5,6-dihydro-dicyclopentadiene.

One mole (191.3 g.) of 5-isothiocyano-5,6-dihydrodicyclopentadiene (prepared in accordance with the procedure disclosed in Journal or Organic Chemistry, 34, 616 (1969)), 4.0 moles (160 g.) of NaOH and 10 moles (180 ml.) of water are charged into a 1.3 liter nickel-lined autoclave. The autoclave is shaken and heated to 255°–260° C.; the pressure is approximately 400 p.s.i. The reaction is continued for 30 minutes after which the autoclave is cooled, emptied and washed with hexane. The resulting mixture is filtered and the solids washed with water and hexane. The filtrate layers are separated, and the aqueous phase is extracted with hexane. The resulting mixture is distilled and the product, 5-amino-5,6-dihydro-dicyclopentadiene, is collected as a substantially pure pale yellow liquid at about 59°–61° C./0.30 mm. Hg. in a typical yield of about 85% of the theoretical yield.

COMPARATIVE EXAMPLE

This comparative example illustrates the attempted hydrolysis of 5-isothiocyano-5,6-dihydro-dicyclopentadiene to 5-amino-5,6-dihydro-dicyclopentadiene at a temperature below the melting point of the thiourea intermediate.

To a stirred solution of 100 g. of 50% aqueous NaOH heated at refluxing temperature (122° C.) is added dropwise over 90 minutes 49.2 g. (0.258 moles) of 5-isothiocyano-5,6-dihydro-dicyclopentadiene. An exothermic reaction occurs and a tan solid separates. So much solid separates that the mixture becomes unstirrable. Analysis of this solid will show it to be 1,3-bis[5,6-dihydro-dicyclopentadienyl)]-2-thiourea having the formula

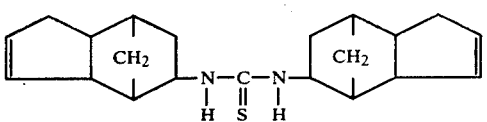

The procedure described above is repeated using 65% NaOH at refluxing temperature with the same results Other features, advantages and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while a specific embodiment of this invention has been described in considerable detail, variations and modifications of the embodiment can be effected without departing from the spirit and scope of the invention as disclosed and claimed.

What I claim and desire to protect by Letters Patent is:

1. The process of preparing 5-amino-5,6-dihydro-dicyclopentadiene, which comprises reacting 5-isothiocyano-5,6-dihydrodicyclopentadiene and an aqueous caustic medium at a temperature in excess of the melting point of 1,3-bis[5-(5,6-dihydro-dicyclopentadienyl)]-2-thiourea while establishing and maintaining a pressure sufficient to maintain the water in the reaction mixture in a liquid state.

* * * * *